US010472686B2

(12) United States Patent
Rey et al.

(10) Patent No.: US 10,472,686 B2
(45) Date of Patent: Nov. 12, 2019

(54) MECHANISMS OF ANTIMICROBIAL SUSCEPTIBILITY

(71) Applicant: Roche Molecular Systems, Inc., Pleasanton, CA (US)

(72) Inventors: Diego Ariel Rey, San Francisco, CA (US); Micah Bodner, Eugene, OR (US); Jeremiah Marsden, Eugene, OR (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/848,391

(22) Filed: Dec. 20, 2017

(65) Prior Publication Data

US 2018/0112281 A1 Apr. 26, 2018

Related U.S. Application Data

(62) Division of application No. 15/161,857, filed on May 23, 2016, now Pat. No. 9,879,328.

(60) Provisional application No. 62/166,964, filed on May 27, 2015.

(51) Int. Cl.
*C12Q 1/6897* (2018.01)
*C12Q 1/66* (2006.01)
*C12Q 1/04* (2006.01)
*C12Q 1/689* (2018.01)
*C12N 7/00* (2006.01)

(52) U.S. Cl.
CPC ............ *C12Q 1/6897* (2013.01); *C12N 7/00* (2013.01); *C12Q 1/04* (2013.01); *C12Q 1/66* (2013.01); *C12Q 1/689* (2013.01); *C12N 2795/10041* (2013.01); *C12N 2795/10043* (2013.01)

(58) Field of Classification Search
CPC .................................................. C12Q 1/6897
See application file for complete search history.

(56) References Cited

U.S. PATENT DOCUMENTS

| 5,736,388 | A | 4/1998 | Chada et al. | |
| 8,066,984 | B2 * | 11/2011 | Szalay .................. | A61K 9/0019 424/93.21 |
| 8,530,178 | B2 | 9/2013 | Sobek et al. | |
| 8,829,473 | B1 | 9/2014 | Griswold et al. | |
| 9,388,453 | B2 * | 7/2016 | Rey .......................... | C12N 1/20 |
| 9,879,328 | B2 | 1/2018 | Rey et al. | |
| 2006/0105915 | A1 | 5/2006 | Naleway et al. | |
| 2009/0155768 | A1 | 6/2009 | Scholl et al. | |
| 2010/0112549 | A1 | 5/2010 | Rey et al. | |
| 2011/0097753 | A1 | 4/2011 | Wang et al. | |
| 2014/0011225 | A1 | 1/2014 | Bhattacharyya et al. | |
| 2014/0099654 | A1 | 4/2014 | Cali et al. | |
| 2015/0064138 | A1 | 3/2015 | Lu et al. | |
| 2015/0104787 | A1 | 4/2015 | Rey et al. | |
| 2015/0218613 | A1 | 8/2015 | De Forest et al. | |
| 2016/0348187 | A1 | 12/2016 | Rey et al. | |

FOREIGN PATENT DOCUMENTS

| WO | 03041483 A2 | 5/2003 |
| WO | 2013086457 A1 | 6/2013 |
| WO | 2014124226 A1 | 8/2014 |
| WO | 2014160418 A2 | 10/2014 |

OTHER PUBLICATIONS

Nordmann, P., L. Poirel, and L. Dortet, Rapid Detection of Carbapenemase-producing Enterobacteriaceae. Emerging Infectious Diseases, 2012. 18(9): p. 1503-1507.
Metzger, S., R.A. Frobel, and W.M. Dunne Jr, Rapid simultaneous identification and quantitation of *Staphylococcus aureus* and Pseudomonas aeruginosa directly from bronchoalveolar lavage specimens using automated microscopy. Diagnostic Microbiology and Infectious Disease, 2014. 79(2): p. 160-165.
Lee, K., et al., Modified Hodge and EDTA-disk synergy tests to screen metallo-β-lactamase-producing strains of Pseudomonas and Acinetobactet species. Clinical Microbiology and Infection, 2001. 7(2): p. 88-91.
Xu et al., "A self-assembled quantum dot probe for detecting b-lactamase activity", "Biochemical and Biophysical Research Communications", 2006, pp. 931-935, vol. 344.
Swezey R.R. et al.: The in vivo rate of glucose-6-phosphate dehydrogenease acivity in sea urchin eggs determined with a photolabile eaged substrate, Developmental Biology vol. 169, No. 2, Jun. 1995, pp. 733-744.
Swezey, R.R. et al., The Use of Caged Substrates to Assess the Activity of 6-Phosphogluconate Dehydrogenase in Living Sea Urchin Eggs, Experimental Cell Research 20 1,366-372 ( 1992).
Price, S.C. et al., Rapid antibiotic susceptibility phenotypic characterization of *Staphylococcus aureus* using automated microscopy of small numbers of cells, Journal of Microbiological Methods 98 (2014) 50-58.
International Search Report & Written Opinion dated Jul. 21, 2016 in Application No. PCT/EP2016/061691, 10 pages.
Kwon et al. Antimicrobial Agents and Chemotherapy, 2006, 50(5): 1623-1627.
Melamed S. et al., Microbial sensor cell arrays, Current Opinion in Biotechnology, Feb. 1, 2012, pp. 2-8, vol. 23, No. 1, Elsevier Ltd.

* cited by examiner

*Primary Examiner* — Bin Shen
(74) *Attorney, Agent, or Firm* — David J. Chang

(57) ABSTRACT

Disclosed herein are methods and compositions for determining the presence or absence of a mechanism of antimicrobial resistance in a sample.

10 Claims, 6 Drawing Sheets

MECHANISMS OF ANTIMICROBIAL SUSCEPTIBILITY

CROSS REFERENCE TO RELATED APPLICATIONS

This application is a divisional of U.S. patent application Ser. No. 15/161,857, filed on May 23, 2016, which claims the benefit of priority of U.S. Provisional Patent Application No. 62/166,964, filed May 27, 2015, and is related to U.S. patent application Ser. No. 14/550,335, filed Nov. 21, 2014; the entire disclosures of all are hereby incorporated by reference, in their entireties, for all purposes.

BACKGROUND OF THE INVENTION

Field of the Invention

The invention relates to methods and compositions for determining mechanisms that impart an antimicrobial susceptibility phenotype of an organism.

Description of the Related Art

The antimicrobial susceptibility phenotype of an organism may be due to a variety of mechanisms including, for example, the expression of various enzymes that deactivate the antimicrobial of interest, or cell surface modifications that prevent entry of the antimicrobial.

Determination of a specific mechanism involved in an antimicrobial susceptibility phenotype can be important for epidemiological analysis and in determining an appropriate therapy. For example, if it is determined that a bacteria is non-susceptible to a β-lactam due to the expression of a β-lactamase enzyme, this information can be used to inform the possibility of administering a therapy that includes a β-lactamase inhibitor. If instead the organism is non-susceptible to the β-lactam and it is determined that the organism does not express the β-lactamase, this information can be used to determine that a β-lactamase inhibitor may not provide a suitable therapy.

Different technologies in the art may be used for determining the specific mechanisms involved in an antimicrobial susceptibility phenotype. For example, nucleic acid amplification techniques (NAA) such as polymerase chain reaction (PCR) can be used for detecting the presence of a gene such as a species-specific gene and a β-lactamase gene. However, such NAA techniques can only infer the possibility an organism expressing the gene. As such, NAA techniques can identify the presence of an identifying nucleic acid sequence or antimicrobial resistance gene of an organism but cannot determine if that gene is expressed and cannot determine the susceptibility of the organism to an antimicrobial.

Colorimetric assays have been developed for the detection of the expression of enzymes that inactivate an antimicrobial agent. The Carba NP test is one such example through which the presence of expressed carbapenemases can be detected due to a color change of a solution (Nordmann, P., L. Poirel, and L. Dortet, *Rapid Detection of Carbapenemase-producing Enterobacteriaceae*. Emerging Infectious Diseases, 2012. 18(9): p. 1503-1507). This test detects the presence of expressed carbapenemases and correlates to the carbapenem susceptibility of an organism. However, the assay cannot determine the identity of the organism and thus requires prior isolation of the organism and cannot determine susceptibility if the mechanism responsible is not enzymatic.

Automated systems exist that provide identification and susceptibility information in an integrated system. The combination of peptide nucleic acid (PNA) fluorescence in situ hybridization (FISH) for organism identification and automated microscopy for the monitoring of the organism's growth rate in the presence of antibiotics is one example of such a system (Metzger, S., R. A. Frobel, and W. M. Dunne Jr, *Rapid simultaneous identification and quantitation of Staphylococcus aureus and Pseudomonas aeruginosa directly from bronchoalveolar lavage specimens using automated microscopy*. Diagnostic Microbiology and Infectious Disease, 2014. 79(2): p. 160-165). However, this system lacks the ability to determine the mechanisms involved in the observed susceptibility phenotype.

Finally, traditional culture techniques may be used to identify organisms and determine the mechanisms involved in imparting a susceptibility phenotype. An example of such an assay is the Modified Hodge Test used for determining the presence of carbapenemases (Lee, K., et al., *Modified Hodge and EDTA-disk synergy tests to screen metallo-β-lactamase-producing strains of Pseudomonas and Acinetobacter species*. Clinical Microbiology and Infection, 2001. 7(2): p. 88-91). However, these techniques rely on observations derived from the antibiotic susceptibility phenotype of an organism and cannot detect the presence of a mechanism involved in the phenotype if the phenotype is not expressed.

The limitations of existing technologies thus requires information from multiple assays and systems in order to provide identification, phenotypic susceptibility determination, and determination of the mechanisms involved in imparting the susceptibility phenotype. Because of this, healthcare providers must purchase and operate different systems in order to acquire this information—a costly and complicated endeavor. Due to these limitations, there is a need for a single assay that provides identification, phenotypic susceptibility determination, and determination of the mechanisms involved in imparting the susceptibility phenotype.

SUMMARY OF THE INVENTION

Disclosed herein are methods and compositions for determining the presence or absence of a mechanism of antimicrobial resistance in a sample. In one embodiment, the present invention relates to a method for determining the presence or absence of a mechanism of antimicrobial resistance in a microorganism that is not susceptible to an antimicrobial in a sample, comprising, providing a sample comprising a microorganism of interest; contacting a portion of said sample with an inhibitor, wherein said inhibitor inhibits a mechanism of conferring non-susceptibility in said microorganism; contacting said portion of said sample comprising said inhibitor with an antimicrobial agent, wherein said antimicrobial agent is a compound that kills, inhibits the growth, or otherwise compromises the viability of one or more microorganisms; contacting said portion of said sample with a live cell reporter capable of generating a detectable signal; and detecting the presence or absence of a signal from said portion of said sample, wherein the presence of said signal indicates that the mechanism of antimicrobial resistance inhibited by said inhibitor is not present in said microorganism, and wherein the absence of said signal indicates that the mechanism of antimicrobial resistance inhibited by said inhibitor is present in said microorganism.

In another embodiment, the present invention relates to a method for determining the presence or absence of a mechanism of antimicrobial resistance in a microorganism in a sample, comprising, providing a sample comprising a microorganism of interest; contacting a first portion of said sample with an antimicrobial agent, wherein said antimicrobial agent is a compound that kills, inhibits the growth, or otherwise compromises the viability of one or more microorganisms; contacting said first portion of said sample with a live cell reporter capable of generating a detectable signal; detecting the presence or absence of a signal from said first portion of said sample comprising said antimicrobial agent and said live cell reporter, wherein the absence of said signal indicates that said microorganism is susceptible to said antimicrobial agent, and wherein the presence of said signal indicates that said microorganism is non-susceptible to said antimicrobial agent; contacting a second portion of said sample with an inhibitor, wherein said inhibitor inhibits a mechanism of conferring non-susceptibility to said antimicrobial agent in said microorganism; contacting said second portion of said sample comprising said inhibitor with said antimicrobial agent; contacting said second portion of said sample with a live cell reporter capable of generating a detectable signal; and detecting the presence or absence of a signal from said second portion of said sample, wherein the presence of said signal indicates that the mechanism of antimicrobial resistance inhibited by said inhibitor is not present in said microorganism, and wherein the absence of said signal indicates that the mechanism of antimicrobial resistance inhibited by said inhibitor is present in said microorganism.

In still another embodiment, the present invention relates to a method for determining the presence or absence of a mechanism of antimicrobial resistance in a microorganism in a sample, comprising, providing a sample comprising a microorganism of interest; contacting a first portion of said sample with an antimicrobial agent and a live cell reporter capable of generating a detectable signal when in the presence of a substrate, wherein said antimicrobial agent is a compound that kills, inhibits the growth of, or otherwise compromises the viability of one or more microorganisms; contacting a second portion of said sample with a caged substrate and a live cell reporter capable of generating a detectable signal, wherein the caged substrate is un-caged by a mechanism associated with a non-susceptibility phenotype to said antimicrobial agent; and detecting the presence or absence of a signal from said first portion and from said second portion, wherein the absence of said signal from said first portion indicates that the microorganism is susceptible to said antimicrobial agent, wherein the presence of said signal from said first portion indicates that the microorganism is non-susceptible to said antimicrobial agent, wherein the presence of said signal from said second portion indicates the presence of said mechanism associated with said non-susceptibility phenotype to said antimicrobial agent, and wherein the absence of said signal from said second portion indicates the absence of said mechanism associated with said non-susceptibility phenotype to said antimicrobial agent.

In another embodiment, the present invention relates to a kit for for determining a mechanism of antimicrobial resistance for a microorganism to an antimicrobial agent comprising, an antimicrobial agent, wherein the antimicrobial agent is a compound that kills, inhibits the growth of, or otherwise compromises the viability of the growth of one or more microorganisms; a non-replicative transduction particle (NRTP) comprising a reporter nucleic acid molecule encoding a reporter molecule; a caged substrate capable of entering the microorganism and becoming an un-caged substrate in the presence of an enzyme related to a mechanism of resistance to the antimicrobial agent, wherein the un-caged substrate reacts with the reporter molecule to produce a detectable signal, wherein detection of the detectable signal confirms a presence of the microorganism in the sample; and instructions for using the antimicrobial agent, the NRTP, and the caged substrate to determine the mechanism of antimicrobial resistance for the microorganism to the antimicrobial agent based on the presence or absence of a detectable indication of viability associated with the microorganism when the microorganism is in contact with the antimicrobial agent, the NRTP and the caged substrate, wherein the presence of a detectable indication of viability indicates that the microorganism is viable and that the enzyme related to the mechanism of resistance to the antimicrobial agent is expressed by the microorganism, and wherein the absence of an indication of viability indicates that the microorganism is not viable and that the enzyme related to the mechanism of resistance to the antimicrobial agent is not expressed by the microorganism.

In yet another embodiment, the present invention relates to a composition comprising a meropenem-caged decanol.

In another embodiment, the present invention relates to an in vitro cell culture, a plurality of cells in the cell culture comprising a non-replicative transduction particle (NRTP) comprising a reporter nucleic acid molecule encoding a reporter molecule; and a caged substrate capable of becoming uncaged in the presence of enzymatic activity associated with a mechanism of antimicrobial resistance, wherein said uncaged substrate is capable of reacting with said reporter molecule to produce a detectable signal.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

I. Definitions

Figure 1:
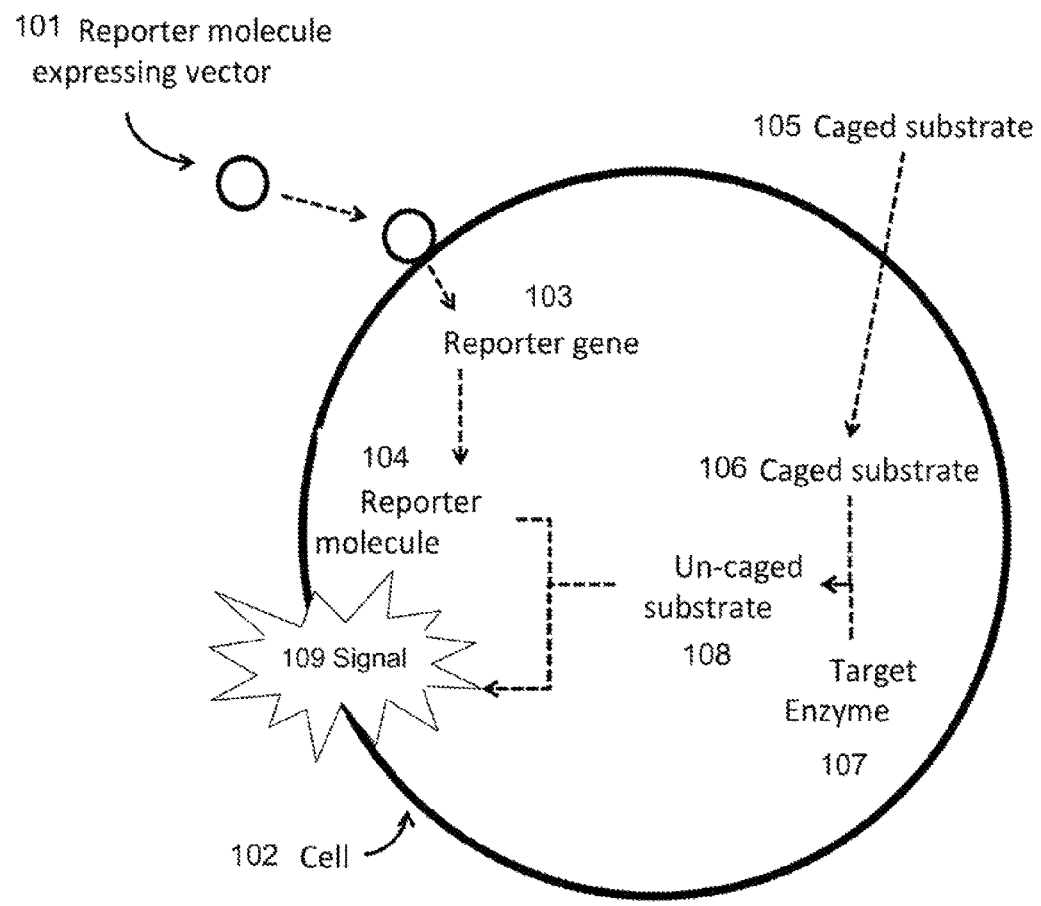
FIG. 1 illustrates a reporter system for the detection of intracellular enzymes within viable cells that employs caged substrate molecules that can be un-caged by a target intracellular enzyme, according to an embodiment.

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

An "antimicrobial susceptibility phenotype" refers to mechanisms that are involved in imparting susceptibility or resistance of an organism to an antimicrobial.

An "antimicrobial agent" refers to a compound that kills or inhibits the growth or otherwise compromises the viability of one or more microorganisms. Antimicrobial agents include antibiotics, antifungals, antiprotozoals, antivirals, and other compounds. "Antimicrobial susceptibility" or "antimicrobial sensitivity" is the susceptibility of microorganisms to antimicrobial agents. "Non-susceptibility" or "antimicrobial non-susceptibility" arises when a microorganism becomes more or fully resistant to antimicrobials which previously could treat it. In certain aspects, antimicrobial non-susceptibility is an antibiotic resistance, which applies to bacteria and antibiotics. Antimicrobial non-susceptibility may arise through different ways: natural resistance in certain types of microorganism, genetic mutation, or by one species acquiring resistance from another. Herein, antimicrobial non-susceptibility can appear spontaneously due to random mutations, or more commonly, following gradual buildup over time, and because of misuse of antibiotics or antimicrobials. Further, all classes or microorganisms may develop antimicrobial non-susceptibility (e.g. fungi and antifungal resistance; viruses and antiviral resistance; protozoa and antiprotozoal resistance; bacteria and antibiotic resistance).

A "transduction particle" refers to a virus capable of delivering a non-viral nucleic acid molecule into a cell. The virus can be a bacteriophage, adenovirus, etc.

A "non-replicative transduction particle" (NRTP) refers to a virus capable of delivering a non-viral nucleic acid molecule into a cell, but does not package its own replicated viral genome into the transduction particle. The virus can be a bacteriophage, adenovirus, etc. NRTPs and methods of making the same are described in detail in PCT/US2014/026536, filed on Mar. 13, 2014, which is incorporated by reference in its entirety.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that surrounds the protein coat. When referring to a virus that infects bacteria, the terms "virus", "phage" and "bacteriophage" are used interchangeably in the specification.

The term "ameliorating" refers to any therapeutically beneficial result in the treatment of a disease state, e.g., a disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term stringent hybridization conditions refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary", "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm. nih.gov/).

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

II. NRTPs and Reporter Assays

Non-replicative transduction particles (NRTPs) and methods of producing NRTPs are described in PCT Application No. PCT/US2014/026536, filed on Mar. 13, 2014 and in U.S. patent application Ser. No. 14/550,335, filed on Nov. 21, 2014, the entire disclosures of both are incorporated by reference in their entireties for all purposes. In some embodiments, NRTPs are produced in a bacterial cell packaging system using Disruption/Complementation-based methods. This non-replicative transduction particle packaging system is based on introducing either a silent mutation or a deletion into a component of the genome of a virus/bacteriophage that is recognized by the viral/phage packaging machinery as the element from which genomic packaging is initiated during viral/phage production. Examples of such an element include the pac-site sequence of pac-type bacteriophages and the cos-site sequence of cos-type bacteriophages.

Because these packaging initiation sites are often found within coding regions of genes that are essential to virus/bacteriophage production, the silent mutation or the deletion is introduced such that the pac-site is no longer recognized as a site of packaging initiation by the viral/phage packaging machinery. At the same time, the mutation or deletion does not disrupt the gene in which the site is encoded. By rendering the packaging site sequence non-functional, the mutated virus/bacteriophage is able to undergo a lytic cycle, but is unable to package its genomic DNA into its packaging unit.

An exogenous reporter nucleic acid molecule, such as plasmid DNA, can be introduced into a host bacteria cell that has been lysogenized with a viral/phage genome with a non-functional packaging initiation site sequence. The exogenous reporter nucleic acid molecule can include a native functional packaging initiation site sequence. The exogenous reporter nucleic acid molecule can be introduced into the host bacteria cell and replicated in the cell. When the mutated virus/bacteriophage is undergoing a lytic cycle, the expressed viral/phage packaging machinery packages the exogenous reporter nucleic acid molecule with the functional packaging initiation site sequence into the viral packaging unit. The viral/phage genome is not packaged into the packaging unit because its packaging initiation site sequence has been mutated.

Therefore, the present invention contemplates the use of a bacterial cell packaging system for packaging a reporter nucleic acid molecule into a NRTP for introduction into a cell, which comprises a host bacteria cell, a first nucleic acid construct inside the host bacteria cell, comprising of a bacteriophage genome having a non-functional packaging initiation site sequence, wherein the non-functional packaging initiation site sequence prevents packaging of the bacteriophage genome into the NRTP, and a second nucleic acid construct inside the host bacteria cell and separate from the first nucleic acid construct, comprising of the reporter nucleic acid molecule having a reporter gene and a functional packaging initiation site sequence for facilitating packaging of a replicon of the reporter nucleic acid molecule into the NRTP, wherein the functional second packaging initiation site sequence on the second nucleic acid construct complements the non-functional packaging initiation site sequence in the bacteriophage genome on the first nucleic acid construct. This results in a NRTP that contains the reporter nucleic acid molecule encoding the reporter gene but lacks the bacteriophage genome.

In some embodiments, constructs of the invention (including NRTPs) comprise a reporter nucleic acid molecule including a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (luxA, luxB, luxAB, luc, ruc, nluc, etc.). Reporter molecules can include a bacterial luciferase, a eukaryotic luciferase, an enzyme suitable for colorimetric detection (lacZ, HRP), a protein suitable for immunodetection, such as affinity peptides (His-tag, 3X-FLAG), a nucleic acid that function as an aptamer or that exhibits enzymatic activity (e.g., aptazyme, DNA-zyme, ribozyme), or a selectable marker, such as an antibiotic resistance gene (ampC, tet(M), CAT, erm). Other reporter molecules known in the art can be used for producing signals to detect target nucleic acids or cells.

Disclosed herein are systems for the detection of intracellular enzymes within viable cells that employs caged substrate molecules that can be un-caged by a target intracellular enzyme, according to an embodiment of the invention.

FIG. 1 depicts the general design and function of an intracellular enzyme detection system. A reporter molecule-expressing vector 101 is delivered to a target cell 102 with a NRTP (not shown). The reporter molecule-expressing vector 101 is able to penetrate the target cell 102 via the NRTP and deliver a reporter molecule gene 103 into the target cell 102, and a reporter molecule 104 can then be expressed from the reporter molecule gene 103. A caged substrate 105 is also added to the target cell 102 and is able to penetrate into the target cell 102. If a target intracellular enzyme 107 is present in the target cell 106, the enzyme 107 is able to remove the caging component of the caged substrate 105, thus producing an un-caged substrate 108. The un-caged substrate 108 can then react with the reporter molecule 104 inside of the cell 102, and the product of this reaction results in a detectable signal 109.

Target cells and enzymes: Target cells can include eukaryotic and prokaryotic cell targets and associated enzymes, including, for example, carbapenemase in Enterobacteriaceae, or β-lactamases in *S. aureus*.

Vector delivery systems: The delivery of the vector containing the recombinant DNA can by performed by abiologic or biologic systems. Including but not limited to liposomes, virus-like particles, transduction particles derived from phage or viruses, and conjugation.

Reporter molecules and caged substrates: Various reporter molecules and caged substrates can be employed as those described in Daniel Sobek, J. R., Enzyme detection system with caged substrates, 2007, Zymera, Inc.

III. Antimicrobial Susceptibility Phenotype Determination

Disclosed herein is an integrated system that provides identification, phenotypic susceptibility determination, and determination of the mechanisms involved in imparting the susceptibility phenotype to an organism. The system is based on a live cell reporter system combined with reagents that inhibit the activity of mechanisms involved in imparting the susceptibility phenotype as well as reagents whose activities are dependent on the mechanisms involved in imparting the susceptibility phenotype.

In an embodiment, a live cell reporter assay specific to a target cell is used to report on the presence of a target organism. The reporter assay employs a reagent for the production of a detectable signal, such that detection of the signal indicates that the target organism is present. The reporter assay can also be run combined with an antimicrobial agent to determine if the organism is non-susceptible to the antimicrobial agent. Additionally, the reporter assay can be run with a variant of the reagent whose activity is dependent on the mechanism involved in imparting the susceptibility phenotype. In an embodiment, the reagent is an inhibitor of the mechanism involved in imparting the susceptibility phenotype. The reporter assay is also run with the antimicrobial agent in combination with a second reagent that inhibits a mechanism involved in imparting the susceptibility phenotype.

An example of results produced using the live cell reporter assay are listed in Table 1 below, where "x" indicates that the reporter assay produced a positive result. Based on these results, the method indicates that Sample 1 contains the target organism that is non-susceptible to the antimicrobial agent. Sample 2 contains the target organism, it is non-susceptible to the antimicrobial agent, and the inhibitor inhibits the mechanism involved in imparting the susceptibility phenotype. Sample 3 contains the target organism that is non-susceptible to the antimicrobial agent and the organism expresses a mechanism that may be responsible for the antimicrobial phenotype. Sample 4 contains the target organism that is non-susceptible to the antimicrobial agent and the organism does not express the mechanism that may be responsible for the antimicrobial phenotype. Sample 5 contains the target organism that is susceptible to the antimicrobial agent. Sample 6 contains the target organism, it is susceptible to the antimicrobial agent and it expresses a mechanism that may be involved in an antimicrobial phenotype; as such, the system may determine if an organism expresses a mechanism involved in a non-susceptible phenotype when an organism exhibits a susceptible phenotype. Finally, Sample 7 does not contain the target organism

TABLE 1

Exemplary results produced from live cell reporter assay

|  | Reporter | Reporter + Antimicrobial | Reporter + Antimicrobial + Inhibitor | Reporter + Reagent |
|---|---|---|---|---|
| Sample 1 | x | x | x | NA |
| Sample 2 | x | x |  | NA |
| Sample 3 | x | x | NA | x |
| Sample 4 | x | x | NA |  |
| Sample 5 | x |  | NA |  |
| Sample 6 | x |  | NA | x |
| Sample 7 |  |  | NA |  |

The reporter assay can be employed with a plurality of different live cell reporter systems, a plurality of different antimicrobial agents, and a plurality of different mechanism-conditional reagents, individually or in combination. By evaluating samples with a series of combinations of the components of the method, information about the types of organisms present in a sample, their antimicrobial susceptibility to various antimicrobials, and the various resistance mechanisms that may be involved in the susceptibility phenotypes can be deduced.

In some embodiments, the method does not require isolation of the organism for the assay to be effective. In other embodiments, the method does not require a culture of the organism. In an embodiment, the method is employed directly from a clinical, environmental, or industrial sample. In an embodiment, assay results are determined within eight hours of running the assay.

Various live cell reporter genes and proteins are known in the art. For example, live cell reporter genes and proteins based on the determination of absorbance, fluorescence or bioluminescence have been developed to monitor cell viability and proliferation. In some aspects, a reporter gene is fused to one or more regulatory elements (e.g. promotors or enhancers) and the amount of the reporter protein expressed may be measured. The selection of the reporter system depends on the target cell to be analyzed, sensitivity needs and the available detection strategy, be it absorbance, fluorescence or bioluminescence. Proteins that traditionally have been used as live cell reporters include β-galactosidase (lacZ), chloramphenyl acetyltransferase (CAT), β-glucuronidase (GUS), fluorescent proteins (green, yellow or red fluorescent protein [GFP, YFP or RFP], respectively) and secretory alkaline phosphatase (SEAP). Further, a variety of luciferases may be used as live cell reporter proteins because of their ultrasensitive detection capacity and wide dynamic range. In such a live cell reporter gene construct, a genetic regulatory element is positioned upstream of a luciferase gene and then the resulting reporter construct is transferred into animal cells, plant cells, bacteria or other microorganisms, e.g., through transfection, transformation, transduction or injection. Expression of the luciferase reporter gene is then measured to quantify the activity of the regulatory element and/or to determine cell viability. Luciferase enzymes can be used as single reporters to study one biological event in a given experiment, but because of their different spectral properties and/or substrates, multiple luciferase enzymes can be combined for multiplex luciferase experiments. In certain aspects, the reporter gene may be selected from the group consisting of genes encoding enzymes mediating luminescence reactions (luxA, luxB, luxAB, luc, rue, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm).

In certain aspects, a reporter nucleic acid molecule encoding a reporter molecule may be packaged into a non-replicative transduction particle (NRTP) for introduction into a target cell, e.g. a microbial or bacterial cell. Herein, a live cell reporter comprises a non-replicative transduction particle (NRTP) comprising a reporter nucleic acid molecule encoding a reporter molecule. More specifically, the NRTP comprises a reporter gene that is operably linked to an inducible promoter that controls the expression of a target gene within a target cell. The reporter nucleic acid molecule can thus be introduced into the target cell via a NRTP. When the NRTP that includes the reporter gene is introduced into the target cell, expression of the reporter gene is possible via induction of the target gene promoter in the reporter nucleic acid molecule. In certain aspects, the live cell reporter comprises a nucleic acid molecule comprising a light-emitting protein-encoding gene. In some aspects, the light-emitting protein-encoding gene is a luciferase gene. Suitable exemplary non-replicative transduction particle packaging systems can be based on disruption of a component of the genome of a virus that is recognized by the viral packaging machinery as the element from which genomic packaging is initiated during viral production. In some aspects, this disruption disrupts a packaging initiation site from a bacteriophage, and also disrupts a terminase function. Examples of the disrupted elements include the pac-site sequence of pac-type bacteriophages and the cos-site sequence of cos-type bacteriophages. When the packaging initiation site sequence within the phage is disrupted, the phage cannot produce functional terminases. In an example, the pac-site is encoded within a pacA gene sequence, and terminase functions require both a functional PacA and PacB. Herein, plasmid DNA is packaged into a phage capsid by complementing said disrupted terminases and including a recognizable packaging initiation site on the plasmid DNA. The bacteriophage can be any bacteriophage, such as an Enterobacteriaceae bacteriophage PI, an S. aureus bacteriophage φ80α or a bacteriophage φ11.

IV. Methods for Determining a Mechanism of Antimicrobial Resistance

In one embodiment a method for determining the presence or absence of a mechanism of antimicrobial resistance in a microorganism that is not susceptible to an antimicrobial in a sample is provided, comprising providing a sample comprising a microorganism of interest; contacting at least a portion of said sample with an inhibitor, wherein said inhibitor inhibits a mechanism of conferring non-susceptibility in said microorganism; contacting said portion of said sample comprising said inhibitor with an antimicrobial agent, wherein said antimicrobial agent is a compound that kills, inhibits the growth, or otherwise compromises the viability of one or more microorganisms; contacting said portion of said sample with a live cell reporter capable of generating a detectable signal; and detecting the presence or absence of a signal from said portion of said sample, wherein the presence of said signal indicates that the mechanism of antimicrobial resistance inhibited by said inhibitor is not present in said microorganism, and wherein the absence of said signal indicates that the mechanism of antimicrobial resistance inhibited by said inhibitor is present in said microorganism.

In another embodiment a method for determining the presence or absence of a mechanism of antimicrobial resistance in a microorganism in a sample is provided, comprising providing a sample comprising a microorganism of interest; contacting a first portion of said sample with an antimicrobial agent, wherein said antimicrobial agent is a compound that kills, inhibits the growth, or otherwise compromises the viability of one or more microorganisms; contacting said first portion of said sample with a live cell reporter capable of generating a detectable signal; detecting the presence or absence of a signal from said first portion of said sample comprising said antimicrobial agent and said live cell reporter, wherein the absence of said signal indicates that said microorganism is susceptible to said antimicrobial agent, and wherein the presence of said signal indicates that said microorganism is non-susceptible to said antimicrobial agent; contacting a second portion of said sample with an inhibitor, wherein said inhibitor inhibits a mechanism of conferring non-susceptibility to said antimicrobial agent in said microorganism; contacting said second portion of said sample comprising said inhibitor with said antimicrobial agent; contacting said second portion of said sample with a live cell reporter capable of generating a detectable signal; and detecting the presence or absence of a signal from said second portion of said sample, wherein the presence of said signal indicates that the mechanism of antimicrobial resistance inhibited by said inhibitor is not present in said microorganism, and wherein the absence of said signal indicates that the mechanism of antimicrobial resistance inhibited by said inhibitor is present in said microorganism. In certain embodiments the method further comprises contacting a third portion of said sample with a live cell reporter capable of generating a detectable signal when in the presence of a caged substrate, wherein said caged substrate is un-caged by a mechanism associated with a non-susceptibility phenotype to said antimicrobial agent; and detecting the presence or absence of a signal from said third portion of said sample, wherein the presence of said signal indicates that the mechanism associated with said non-susceptibility phenotype to said antimicrobial agent is present in said microorganism, and wherein the absence of said signal indicates that the mechanism associated with said non-susceptibility phenotype to said antimicrobial agent is not present in said microorganism.

In certain embodiments of these methods said inhibitor comprises a metal chelator or a beta lactamase inhibitor. In some embodiments said metal chelator is EDTA. In some embodiments, said beta lactamase inhibitor is boronic acid. In some embodiments said metal chelator is EDTA and said beta lactamase inhibitor is boronic acid.

In another embodiment, a method for determining the presence or absence of a mechanism of antimicrobial resistance in a microorganism in a sample is provided, comprising providing a sample comprising a microorganism of interest; contacting a first portion of said sample with an antimicrobial agent and a live cell reporter capable of generating a detectable signal when in the presence of a substrate, wherein said antimicrobial agent is a compound that kills, inhibits the growth of, or otherwise compromises the viability of one or more microorganisms; contacting a second portion of said sample with a caged substrate and a live cell reporter capable of generating a detectable signal, wherein the caged substrate is un-caged by a mechanism associated with a non-susceptibility phenotype to said antimicrobial agent; and detecting the presence or absence of a signal from said first portion and from said second portion, wherein the absence of said signal from said first portion indicates that the microorganism is susceptible to said antimicrobial agent, wherein the presence of said signal from said first portion indicates that the microorganism is non-susceptible to said antimicrobial agent, wherein the presence of said signal from said second portion indicates the presence of said mechanism associated with said non-susceptibility phenotype to said antimicrobial agent, and wherein the absence of said signal from said second portion indicates the absence of said mechanism associated with said non-susceptibility phenotype to said antimicrobial agent.

In certain embodiments, said caged substrate comprises a fatty aldehyde. In some embodiments, said caged substrate comprises a fatty aldehyde caged by an antimicrobial agent-based molecule. In some embodiments, said fatty aldehyde is uncaged upon contacting an enzyme that reacts with said caged molecule in a manner that allows said fatty aldehyde to interact with said reporter molecule to produce said signal. In particular embodiments, said enzyme is a carbapenemase. In some embodiments, said caged substrate comprises a fatty aldehyde caged by a meropenem-based molecule. In certain embodiments, said fatty aldehyde is decanal. In certain embodiments, said fatty aldehyde is uncaged upon contacting a carbapenemase, allowing said fatty acid to interact with said reporter molecule to produce said signal. In some embodiments, said caged substrate is encapsulated in a liposome.

In certain embodiments of the above methods, contacting said sample with said live cell reporter comprises introducing into said sample a non-replicative transduction particle comprising a reporter gene encoding a reporter molecule and lacking a bacteriophage genome under conditions such that said non-replicative transduction particle can transduce said microorganism and wherein said reporter gene can be expressed in said microorganism; and providing conditions for activation of said reporter molecule. In some embodiments, said reporter gene is selected from the group consisting of genes encoding enzymes mediating luminescence reactions, genes encoding enzymes mediating colorimetric reactions, genes encoding fluorescent proteins, genes encoding selectable markers, and nucleic acid molecules encoding affinity peptides. In certain embodiments, said reporter gene is operatively linked to a constitutive promoter. In some embodiments, said reporter gene is selected from the group consisting of genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). In certain embodiments, said genes encoding enzymes mediating luminescence reactions comprise genes encoding one or more luciferases. In certain embodiments, said live cell reporter comprises a nucleic acid molecule comprising a light-emitting protein-encoding gene. In certain embodiments, said light-emitting protein-encoding gene is a luciferase gene.

In some embodiments, said reporter signal can be detected from a sample at a limit of detection (LoD) of less than 1,000 colony forming units (CFU). In some embodiments, said reporter signal can be detected from a sample at a limit of detection (LoD) of less than 100 colony forming units (CFU). In some embodiments, said reporter signal can be detected from a sample at a limit of detection (LoD) of less than 10 colony forming units (CFU). In some embodiments, said reporter signal can be detected from a sample at a LoD less than five CFU. In some embodiments, said reporter signal can be detected from a sample at a LoD of three or less CFU.

In certain embodiments of the above methods said antimicrobial agent is selected from the group consisting of: β-lactams, extended-spectrum β-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Streptogramins, Sulfonamides, Tetracyclines, Rifampicin, mycobacterial antibiotics, Chloramphenicol, and Mupirocin.

In certain embodiments of the above methods said microorganism is a prokaryote or a eukaryote. In some embodiments, said prokaryote are Gram-negative bacteria or Gram-positive bacteria. In some embodiments, said microorganism is *Staphylococcus* spp., Enterobacteriaceae, *Enterococcus* spp. *Streptococcus* spp., *Acinetobacter* spp., *Pseudomonas* spp., *Stenotrophomonas* spp., and *Mycobacterium* spp., or *Candida*.

In certain embodiments, said mechanism of antimicrobial resistance comprises beta-lactamase activity or carbapenemase activity. In some embodiments, said carbapenemase activity is from a Class A carbapenemase, a Class B carbapenemase, a class D carbapenemase, or a combination thereof. In some embodiments, said antimicrobial resistance comprises resistance to a carbapenem.

In another embodiment, a method for determining the presence or absence of a mechanism of antimicrobial resistance in a microorganism in a sample is provided, comprising providing a sample comprising a microorganism of interest; contacting said sample with a live cell reporter capable of generating a detectable signal, an antimicrobial agent, and an inhibitor, wherein said inhibitor is capable of inhibiting a mechanism of resistance to said antimicrobial agent; and detecting the presence or absence of said signal, wherein the absence of said signal indicates the presence of said mechanism of antimicrobial resistance, and wherein the presence of said signal indicates the absence of said mechanism of antimicrobial resistance.

In another embodiment, a method for determining the presence or absence of a mechanism of antimicrobial resistance in a microorganism in a sample is provided, comprising providing a sample comprising a microorganism of interest; contacting a first portion of said sample with a live cell reporter capable of generating a detectable signal; contacting said first portion of said sample with an antimicrobial agent; and detecting the presence or absence of said signal in said first portion, wherein the presence of said signal indicates said microorganism comprises a non-susceptible phenotype, and wherein the absence of said signal indicates said microorganism comprises a susceptible phenotype.

In certain embodiments the method further comprises contacting said first portion of said sample comprising said live cell reporter, said antimicrobial agent, and said microorganism comprising a resistant phenotype with an inhibitor capable of inhibiting a mechanism of resistance to said antimicrobial agent; and detecting the presence or absence of said signal in said first portion, wherein the absence of said signal indicates the presence of a type of said mechanism of antimicrobial resistance in said microorganism comprising a resistant phenotype, and wherein the presence of said signal indicates the absence of said type of said mechanism of antimicrobial resistance in said microorganism.

In certain embodiments, the method further comprises contacting a second portion of said sample comprising with a live cell reporter and a caged substrate under conditions such that the caged substrate enters microorganism, wherein the caged substrate is capable of becoming uncaged in the presence of enzymatic activity associated with the mechanism of antimicrobial resistance, and wherein said uncaged substrate is capable of reacting with said live cell reporter to produce said detectable signal, wherein said live cell reporter will not produce said detectable signal in the absence of said uncaged substrate; and detecting the presence or absence of said signal in said second portion, wherein the presence of said signal indicates the presence of said mechanism of antimicrobial resistance, and wherein the absence of said signal indicates the absence of said mechanism of antimicrobial resistance.

In certain embodiments, the method further comprises contacting a second portion of said sample with a live cell reporter and a caged substrate under conditions such that the caged substrate enters microorganism, wherein the caged substrate is capable of becoming uncaged in the presence of enzymatic activity associated with the mechanism of antimicrobial resistance, wherein said uncaged substrate is capable of reacting with said reporter molecule to produce said detectable signal, and wherein said live cell reporter will not produce said detectable signal in the absence of said uncaged substrate; and detecting the presence or absence of said signal, wherein the presence of said signal indicates the presence of said mechanism of antimicrobial resistance, and wherein the absence of said signal indicates the absence of said mechanism of antimicrobial resistance.

In certain embodiments, the method further comprises contacting a second portion of said sample with a live cell reporter and a caged substrate under conditions such that the caged substrate enters microorganism, wherein the caged substrate is capable of becoming uncaged in the presence of enzymatic activity associated with the mechanism of antimicrobial resistance, wherein said uncaged substrate is capable of reacting with said reporter molecule to produce said detectable signal, and wherein said live cell reporter will not produce said detectable signal in the absence of said uncaged substrate; contacting said second portion with an inhibitor capable of inhibiting a mechanism of resistance to said antimicrobial agent; and detecting the presence or absence of said signal, wherein the absence of said signal indicates the presence of a type of said mechanism of antimicrobial resistance in said microorganism comprising a resistant phenotype, and wherein the presence of said signal indicates the absence of said type of said mechanism of antimicrobial resistance in said microorganism.

In certain embodiments of these methods, said antimicrobial agent is selected from the group consisting of: β-lactams, extended-spectrum β-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Streptogramins, Sulfonamides, Tetracyclines, Rifampicin, mycobacterial antibiotics, Chloramphenicol, and Mupirocin. In certain embodiments, said inhibitor comprises a metal chelator or a beta lactamase inhibitor. In certain embodiments, said metal chelator is EDTA. In certain embodiments, said beta lactamase inhibitor is boronic acid. In certain embodiments, said live cell reporter comprises a nucleic acid molecule comprising a light-emitting protein-encoding gene. In certain embodiments, said light-emitting protein-encoding gene is a luciferase gene. In certain embodiments, said caged substrate comprises a fatty aldehyde. In certain embodiments, said caged substrate comprises a fatty aldehyde caged by a meropenem-based molecule. In certain embodiments, said fatty aldehyde is decanal. In certain embodiments, said fatty aldehyde is uncaged upon contacting a carbapenemase, allowing said fatty acid to interact with said reporter molecule to produce said signal. In certain embodiments, said caged substrate is encapsulated in a liposome.

In another embodiment, a method for determining the presence or absence of a mechanism of antimicrobial resistance in a microorganism in a sample is provided, comprising providing a sample comprising a microorganism of interest; contacting the sample with a live cell reporter; contacting the sample with a caged substrate under conditions such that the caged substrate enters microorganism, wherein the caged substrate is capable of becoming uncaged in the presence of enzymatic activity associated with a mechanism of antimicrobial resistance, and wherein said uncaged substrate is capable of reacting with said reporter molecule to produce a detectable signal; and detecting the presence or absence of said signal, wherein the presence of said signal indicates the presence of said enzymatic activity associated with a mechanism of antimicrobial resistance in said microorganism of interest, and wherein the absence of said signal indicates the absence of said enzymatic activity associated with a mechanism of antimicrobial resistance in said microorganism of interest.

In certain embodiments, said live cell reporter comprises a non-replicative transduction particle (NRTP) comprising a reporter nucleic acid molecule encoding a reporter molecule. In certain embodiments, the method further comprises contacting said sample with an antimicrobial agent to determine whether said microorganism is resistant to said antimicrobial agent. In certain embodiments, said sample is contacted with the antimicrobial agent prior to contacting the sample with the live cell reporter. In certain embodiments, said sample is contacted with the live cell reporter prior to contacting the sample with the antimicrobial agent. In certain embodiments, said antimicrobial agent is selected from the group consisting of: β-lactams, extended-spectrum β-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Streptogramins, Sulfonamides, Tetracyclines, Rifampicin, mycobacterial antibiotics, Chloramphenicol, and Mupirocin.

In certain embodiments, said microorganism is a prokaryote or a eukaryote.

In certain embodiments, said microorganism is a Gram-negative bacteria.

In certain embodiments, said microorganism is *Staphylococcus* spp., Enterobacteriaceae, *Enterococcus* spp. *Streptococcus* spp., *Acinetobacter* spp., *Pseudomonas* spp., *Stenotrophomonas* spp., and *Mycobacterium* spp., or *Candida*.

In certain embodiments, said microorganism of interest is resistant to at least one antimicrobial agent. In certain embodiments, said live cell reporter comprises a nucleic acid molecule comprising a light-emitting protein-encoding gene. In certain embodiments, said light-emitting protein-encoding gene is a luciferase gene. In certain embodiments, said enzymatic activity comprises beta-lactamase activity. In certain embodiments, said enzymatic activity comprises carbapenemase activity. In certain embodiments, said carbapenemase activity is from a Class A carbapenemase, a Class B carbapenemase, a class D carbapenemase, or a combination thereof.

In certain embodiments, said caged substrate comprises a fatty aldehyde. In certain embodiments, the caged substrate comprises a fatty aldehyde caged by a meropenem-based molecule. In certain embodiments, said fatty aldehyde is decanal. In certain embodiments, said fatty aldehyde is uncaged upon contacting a carbapenemase, allowing said fatty acid to interact with said reporter molecule to produce said signal. In certain embodiments, the caged substrate is encapsulated in a liposome. In certain embodiments, said antimicrobial resistance comprises resistance to a carbapenem. In certain embodiments, said carbapenem comprises ertapenem.

In certain embodiments, the method further comprises contacting the sample with an inhibitor suspected of reducing the activity of said enzyme; and detecting the presence or absence of said signal, wherein a reduction of said signal due to addition of said inhibitor as compared to the signal in the absence of said inhibitor indicates the presence and activity of said enzyme associated with a mechanism of antimicrobial resistance in said microorganism of interest. In certain embodiments, said inhibitor comprises a metal chelator or a beta lactamase inhibitor. In certain embodiments, said metal chelator is EDTA. In certain embodiments, said beta lactamase inhibitor is boronic acid.

In another embodiment, a method for determining the presence or absence of an enzyme correlated with a mechanism of antimicrobial resistance in a microorganism in a sample is provided comprising providing a sample comprising a microorganism of interest; contacting the sample with a caged substrate, the caged substrate capable of becoming uncaged upon contact with an active enzyme associated with a mechanism of antimicrobial resistance, wherein said uncaged substrate is capable of producing a signal; contacting the sample with an inhibitor targeting said enzyme, wherein said inhibitor reduces the activity of said enzyme; and detecting the presence or absence of said signal, wherein the absence or reduction of said signal indicates inhibition of the activity of said enzyme associated with a mechanism of antimicrobial resistance in said microorganism of interest.

In another embodiment, a method of detecting the presence or absence of a microorganism in a sample is provided, comprising contacting the sample with a caged substrate, the caged substrate capable of becoming uncaged due to enzymatic activity associated with said microorganism, wherein said uncaged substrate is capable of producing a signal; and detecting the presence or absence of said signal, wherein the presence of said signal indicates the presence of said microorganism in said sample, and wherein the absence of said signal indicates the absence of said microorganism in said sample.

In another embodiment, a method for determining a mechanism of antimicrobial resistance, comprising providing a sample comprising an Enterobacteriaceae; contacting the sample with carbapenem; contacting the sample with a non-replicative transduction particle (NRTP) comprising a luciferase gene encoding a luciferase; contacting the sample with a decanal molecule caged by a meropenem-based molecule, under conditions such that the caged decanal enters the Enterobacteriaceae and becomes un-caged in the presence of carbapenemase, wherein the un-caged decanal reacts with the luciferase to produce a detectable signal, wherein detection of the detectable signal confirms a presence of a carbapenemase-based resistance mechanism in the Enterobacteriaceae in the sample. In certain embodiments, the method further comprises contacting said sample with boronic acid, wherein the reduction of said detectable signal after contacting said sample with boronic acid confirms the presence of a Class A carbapenemase resistance mechanism in the Enterobacteriaceae in the sample. In certain embodiments, the method further comprises contacting said sample with EDTA, wherein the reduction of said detectable signal after contacting said sample with EDTA confirms the presence of a Class B carbapenemase resistance mechanism in the Enterobacteriaceae in the sample.

V. Compositions, Microorganisms and Kits

In one aspect, a composition is provided comprising a meropenem-caged decanal.

In another aspect, a microorganism is provided comprising a non-replicative transduction particle (NRTP) comprising a reporter nucleic acid molecule encoding a reporter molecule; and a caged substrate capable of becoming uncaged in the presence of enzymatic activity associated with a mechanism of antimicrobial resistance, wherein said uncaged substrate is capable of reacting with said reporter molecule to produce a detectable signal. In certain aspects, the microorganism further comprises an antimicrobial agent. In certain aspects, the microorganism further comprises an inhibitor of said enzymatic activity associated with said mechanism of antimicrobial resistance.

In one embodiment, an in vitro cell culture is provided comprising a plurality of cells in the cell culture comprising a non-replicative transduction particle (NRTP) comprising a reporter nucleic acid molecule encoding a reporter molecule; and a caged substrate capable of becoming uncaged in the presence of enzymatic activity associated with a mechanism of antimicrobial resistance, wherein said uncaged substrate is capable of reacting with said reporter molecule to produce a detectable signal. In certain aspects, said plurality of cells further comprises an antimicrobial agent. In certain aspects, said plurality of cells further comprises an inhibitor of said enzymatic activity associated with said mechanism of antimicrobial resistance.

In another embodiment, a kit for determining a mechanism of antimicrobial resistance for a microorganism to an antimicrobial agent is provided comprising an antimicrobial agent, wherein the antimicrobial agent is a compound that kills, inhibits the growth of, or otherwise compromises the viability of the growth of one or more microorganisms; a non-replicative transduction particle (NRTP) comprising a reporter nucleic acid molecule encoding a reporter molecule; a caged substrate capable of entering the microorganism and becoming an un-caged substrate in the presence of an enzyme related to a mechanism of resistance to the antimicrobial agent, wherein the un-caged substrate reacts with the reporter molecule to produce a detectable signal, wherein detection of the detectable signal confirms a presence of the microorganism in the sample; and instructions for using the antimicrobial agent, the NRTP, and the caged substrate to determine the mechanism of antimicrobial resistance for the microorganism to the antimicrobial agent based on the presence or absence of a detectable indication of viability associated with the microorganism when the microorganism is in contact with the antimicrobial agent, the NRTP and the caged substrate, wherein the presence of a detectable indication of viability indicates that the microorganism is viable and that the enzyme related to the mechanism of resistance to the antimicrobial agent is expressed by the microorganism, and wherein the absence of an indication of viability indicates that the microorganism is not viable and that the enzyme related to the mechanism of resistance to the antimicrobial agent is not expressed by the microorganism.

In certain aspects and embodiments of the microorganism, cell culture and kit, said caged substrate comprises a fatty aldehyde. In some embodiments, said caged substrate comprises a fatty aldehyde caged by an antimicrobial agent-based molecule. In some embodiments, said fatty aldehyde is uncaged upon contacting an enzyme that reacts with said caged molecule in a manner that allows said fatty aldehyde to interact with said reporter molecule to produce said signal. In particular embodiments, said enzyme is a carbapenemase. In some embodiments, said caged substrate comprises a fatty aldehyde caged by a meropenem-based molecule. In certain embodiments, said fatty aldehyde is decanal. In certain embodiments, said fatty aldehyde is uncaged upon contacting a carbapenemase, allowing said fatty acid to interact with said reporter molecule to produce said signal. In some embodiments, said caged substrate is encapsulated in a liposome.

In some embodiments, said reporter nucleic acid molecule is selected from the group consisting of genes encoding enzymes mediating luminescence reactions, genes encoding enzymes mediating colorimetric reactions, genes encoding fluorescent proteins, genes encoding selectable markers, and nucleic acid molecules encoding affinity peptides. In certain embodiments, said reporter nucleic acid molecule is operatively linked to a constitutive promoter. In some embodiments, said reporter nucleic acid molecule is selected from the group consisting of genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). In certain embodiments, said genes encoding enzymes mediating luminescence reactions comprise genes encoding one or more luciferases. In certain embodiments, said live cell reporter comprises a nucleic acid molecule comprising a light-emitting protein-encoding gene. In certain embodiments, said light-emitting protein-encoding gene is a luciferase gene.

In certain embodiments said antimicrobial agent is selected from the group consisting of: β-lactams, extended-spectrum β-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Streptogramins, Sulfonamides, Tetracyclines, Rifampicin, mycobacterial antibiotics, Chloramphenicol, and Mupirocin. In certain embodiments said microorganism is a prokaryote or a eukaryote. In some embodiments, said prokaryote are Gram-negative bacteria or Gram-positive bacteria. In some embodiments, said microorganism is *Staphylococcus* spp., Enterobacteriaceae, *Enterococcus* spp. *Streptococcus* spp., *Acinetobacter* spp., *Pseudomonas* spp., *Stenotrophomonas* spp., and *Mycobacterium* spp., or *Candida*. In certain embodiments, said mechanism of antimicrobial resistance comprises beta-lactamase activity or carbapenemase activity. In some embodiments, said carbapenemase activity is from a Class A carbapenemase, a Class B carbapenemase, a class D carbapenemase, or a combination thereof. In some embodiments, said antimicrobial resistance comprises resistance to a carbapenem.

EXAMPLES

Example 1: Detection of NDM-1 via an EDTA inhibitor

Carbapenem non-susceptibility may be imparted by carbapenemase enzymes as well as by other mechanisms including over expression of non-carbapenemase β-lactamase enzymes and porin mutations. Carbapenemases are derived from the classes including A, B, and D. Class A carbapenemases include those encoded by the KPC (*K. pneumoniae* carbapenemase) genes and are susceptible to inhibition by β-lactamase inhibitors. Class B carbapenemases include those encoded by the IMP-type (metallo-β-lactamases), New Delhi metallo-β-lactamase (NDM-1), and VIM (Verona integron-encoded metallo-β-lactamase) genes and require ionic metal to function. Class D carbapenemases include those encoded by the OXA (oxacillinase) genes and are not susceptible to inhibition by β-lactamase inhibitors.

An NDM-1 detection assay is produced using a luciferase-expressing non-replicative transduction particle specific to Enterobacteriaceae (as described in PCT/US2014/026536, Example 1), ertapenem, and the chelator Ethylenediaminetetraacetic acid (EDTA).

A culture of a clinical isolate of an NDM-1-expressing *E. coli* was prepared in LB media and used to determine the response of the NRTP reporter in the presence of ertapenem, EDTA, and Zinc. The assay was prepared by mixing 50 μL of the cell culture at an OD600 of 0.02 to 50 μL of LB media and 100 μL of NRTP reagent prepared in a microwell plate. The assay was incubated for 2 hours at 37° C. under the following conditions: (1) No additives, (2) with the addition of ertapenem at 0.25 μg/mL, (3) with the addition of ertapenem and EDTA at 750 μg/mL, and (4) with the addition of ertapenem and Zinc sulfate at 70 μg/mL. After the incubation, the samples were assayed for luminescence after the injection of a nonanal reagent as a substrate for the live cell reporter using a Molecular Devices SpectraMax L luminometer.

Figure 2:
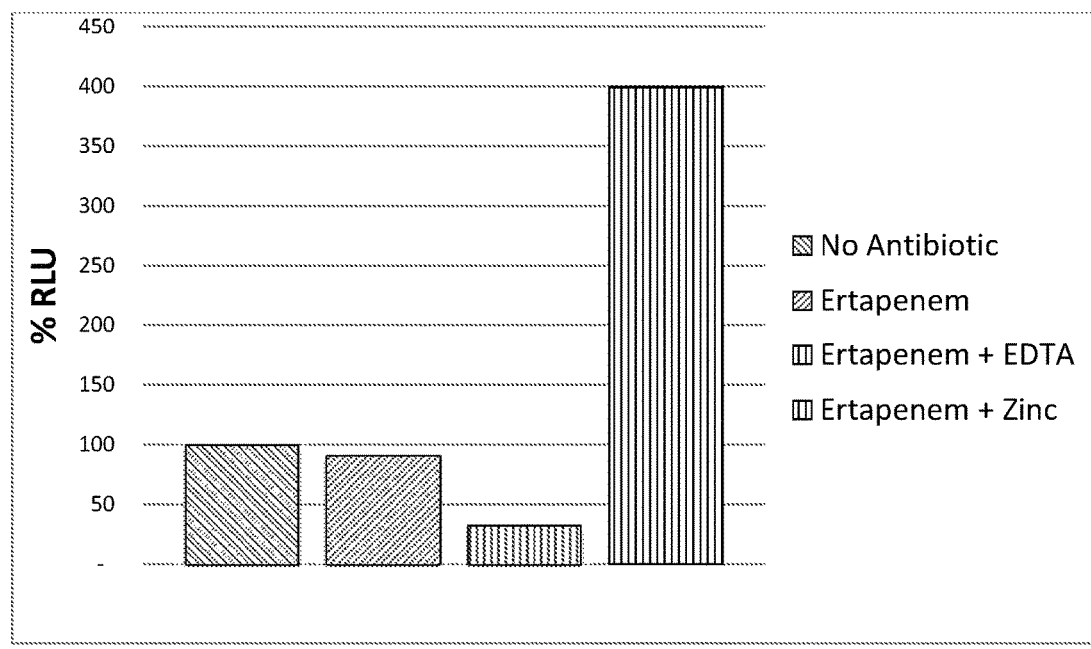
FIG. 2 shows % RLU signal from NRTP detection of NDM-1-expressing *E. coli* in the presence of various additives, normalized to signal from No Antibiotic.
Figure 3:
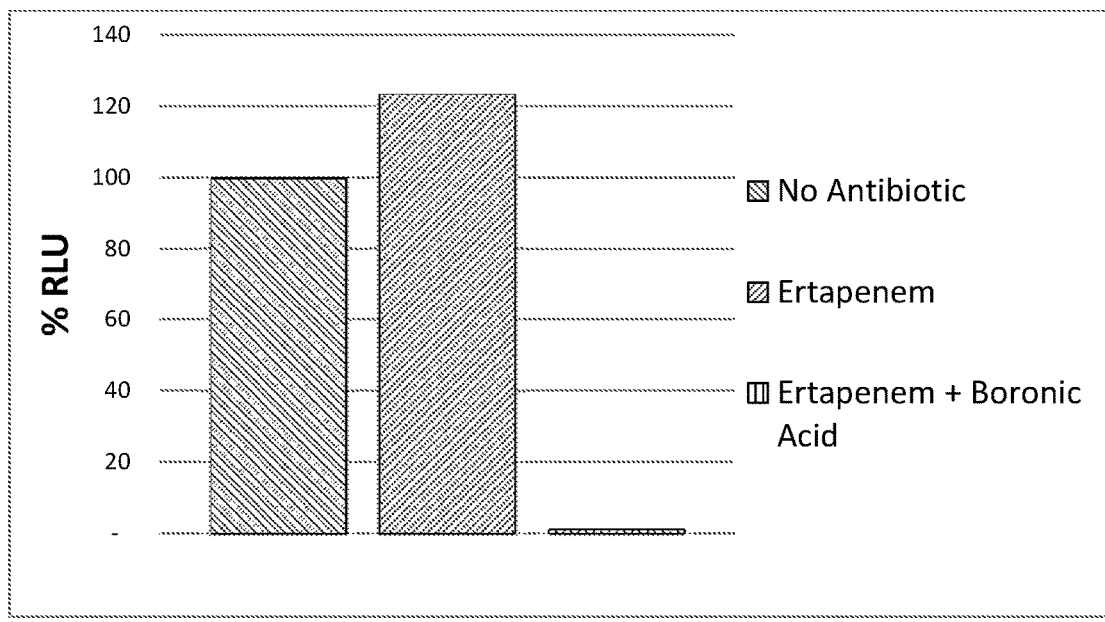
FIG. 3 shows % RLU signal from NRTP detection of KPC-expressing *E. coli* in the presence of various additives, normalized to signal from No Antibiotic

The luminescence readings were then normalized to those produced by sample (1) and plotted as a percentage relative to sample (1) as shown in FIG. 2.

From the results depicted in FIG. 2, it can be seen that the NDM-1-expressing *E. coli* was non-susceptible to ertapenem, since the luminescence signal was not significantly decreased in the presence of the ertapenem. The signal was significantly decreased in the presence of EDTA, indicating that the mechanism involved in the ertapenem non-susceptibility phenotype (i.e. NDM-1) was inhibited in the presence of the chelating agent. Conversely, upon the addition of Zinc to the assay, the signal was significantly increased, again indicative of the role of NDM-1 in imparting the ertapenem non-susceptibility phenotype.

Example 2: Detection of KPC via a Boronic Acid Inhibitor

In another embodiment of the invention, a KPC detection assay is produced using a luciferase-expressing non-replicative transduction particle specific to Enterobacteriaceae as described in PCT/US2014/026536, Example 1, ertapenem and the β-lactamase inhibitor boronic acid.

A culture of a clinical isolate of a KPC-expressing *E. coli* was prepared in LB media and used to determine the response of the NRTP reporter in the presence of ertapenem, and boronic acid. The replicates of the assay were prepared mixing 50 μL of the cell culture at an OD600 of 0.02 to 50 μL of LB media and 100 μL of NRTP reagent prepared in a microwell plate. The assay was incubated for 2 hours at 37° C. under the following conditions: (1) No additives, (2) with the addition of ertapenem at 1 μg/mL, and (3) with the addition of ertapenem and phenyl boronic acid 400 μg/mL. After the incubation, the samples were assayed for luminescence after the injection of a nonanal reagent as a substrate for the live cell reporter using a Molecular Devices SpectraMax L luminometer.

The luminescence readings were then normalized to those produced by sample (1) and plotted as the average percentage relative to sample (1) as shown in FIG. 1.

From the results depicted in FIG. 2, it can be seen that the KPC-expressing *E. coli* was non-susceptible to ertapenem, since the luminescence signal was not significantly decreased in the presence of the ertapenem and in fact the average signal was higher than that without ertapenem. The signal was significantly decreased in the presence of boronic acid, indicating that the mechanism involved in the ertapenem non-susceptibility phenotype (i.e. KPC) was inhibited in the presence of the β-lactamase inhibitor.

Example 3: Determination of Carbapenem Susceptibility Mechanism

A carbapenem susceptibility detection system (for determining antimicrobial susceptibility phenotype) is produced based on a bacterial luciferase-expressing non-replicative transduction particle (NRTP) specific to Enterobacteriaceae, and a caged luciferase substrate that may be un-caged by a carbapenemase enzyme.

Figure 4:
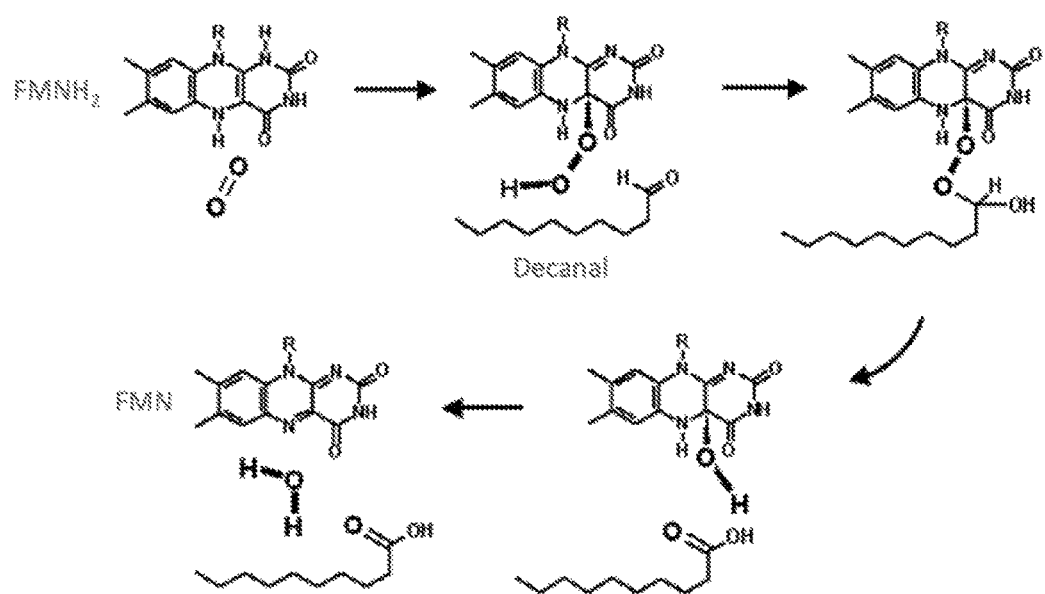
FIG. 4 illustrates a bacterial luciferase-mediated luminescence reaction, according to an embodiment.

The bacterial luciferase luminescence reaction requires the bacterial luciferase enzyme LuxAB, reduced flavin mononucleotide FMNH2, a fatty aldehyde such as decanal, and molecular oxygen (FIG. 4). In this reaction, the luciferase enzyme first binds to FMNH2 and mediates a reaction between FMNH2 and molecular oxygen. Next, a fatty aldehyde, such as decanal, reacts with this complex and causes oxidation of both FMNH2 and decanal, resulting in a photon emission.

Fatty aldehydes such as decanal can be caged by linking to them a molecule (such as a meropenem-based molecule). When caged, the fatty aldehyde is unable to mediate a luminescence reaction. When un-caged, the aldehyde is able to mediate a luminescence reaction. A caged fatty aldehyde can be designed to become un-caged in the presence of an enzyme that hydrolyses the caging element.

A reporter system is designed to detect the presence of at least one intracellular enzyme within viable cells that mediates the un-caging of the caged molecule by one or more target intracellular enzyme (as described in PCT/US2014/026536, paragraphs 196-203). In short, a reporter molecule-expressing nucleic acid (e.g. a vector) may be delivered to a target cell with a non-replicative transduction particle (NRTP). Herein, the reporter molecule-expressing nucleic acid is able to penetrate the target cell via the NRTP and deliver a reporter molecule gene into the target cell and a reporter molecule can then be expressed from the reporter molecule gene. A caged substrate is also added to the target cell and is able to penetrate into the target cell. If a target intracellular enzyme is present in the target cell, the enzyme is able to remove the caging component of the caged substrate, thus producing an un-caged substrate. The un-caged substrate can then react with the reporter molecule inside of the cell, and the product of this reaction results in a detectable signal. Herein, target cells can include eukaryotic and prokaryotic cell targets and associated enzymes, including, for example, β-lactamases in *S. aureus*. The delivery of the reporter molecule-expressing nucleic acid containing the recombinant DNA can by performed by a biologic or biologic systems including but not limited to liposomes, virus-like particles, transduction particles derived from phage or viruses, and conjugation. Further, various reporter molecules and caged substrates can be employed as those described in Daniel Sobek, J. R., *Enzyme detection system with caged substrates*, 2007, Zymera, Inc. In certain aspects, a reporter molecule-expressing vector can be carried by a NRTP, such that the vector can be delivered into a bacterial cell. The reporter molecule to be expressed can be Renilla luciferase, and the caged substrate can be Renilla luciferin that is caged, such that a β-lactamase enzyme that is endogenous to the target cell is able to cleave the caging compound from the caged luciferin and release un-caged luciferin. In this manner, when a target cell that contains the β-lactamase is exposed to the NRTP and caged luciferin, the cell will exhibit a luminescent signal that is indicative of the presence of the β-lactamase present in the cell.

If the target enzyme is present in a cell expressing bacterial luciferase and the caged fatty aldehyde is applied to the sample containing the cell, the enzyme can un-cage the fatty aldehyde, allowing for a luminescence reaction to occur, which produces a detectable luminescence signal. If the target enzyme is not present in the cell, the system does not produce a detectable signal.

Figure 5:
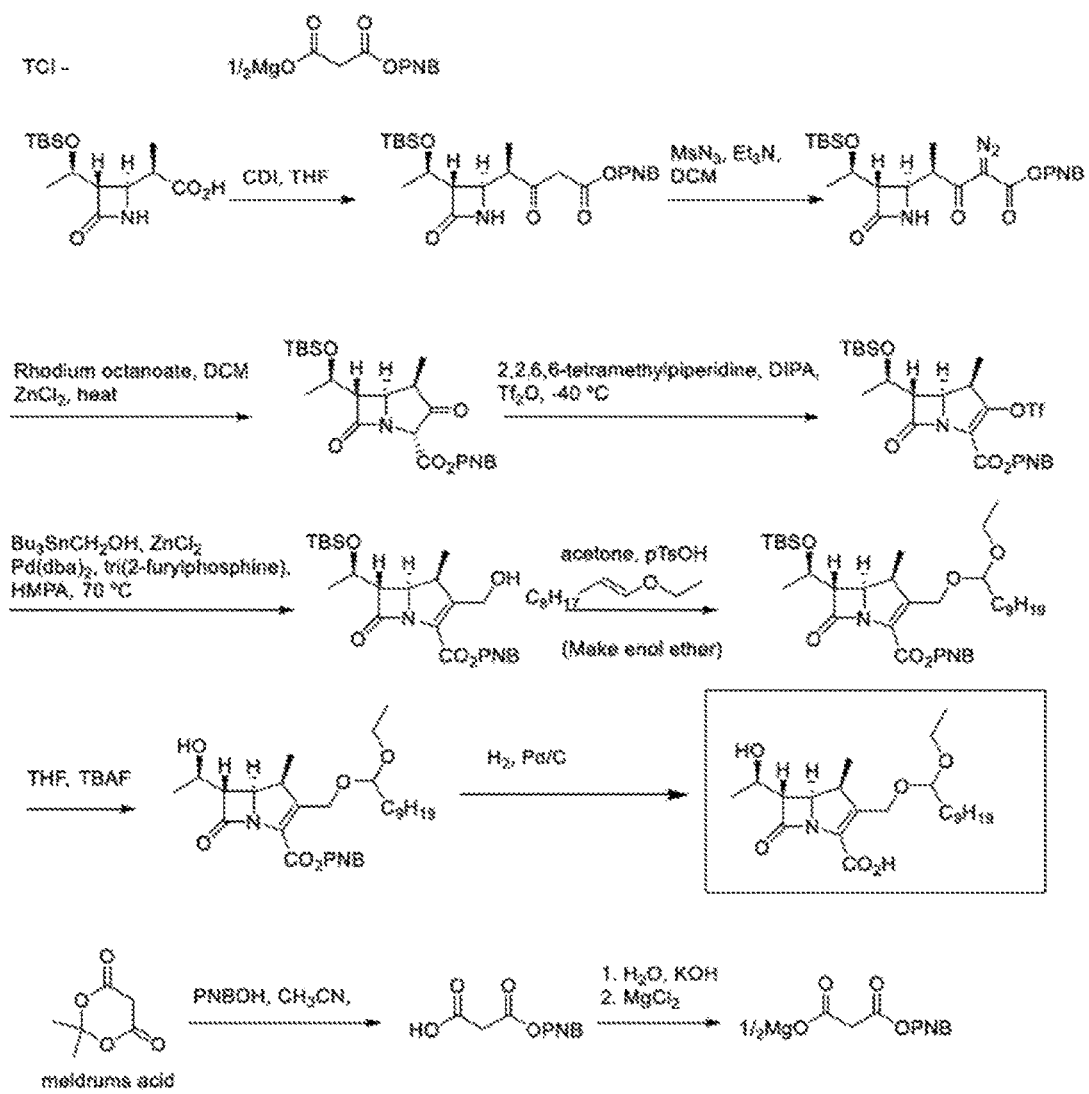
FIG. 5 illustrates the synthesis of a meropenem-caged decanal, according to an embodiment.
Figure 6:
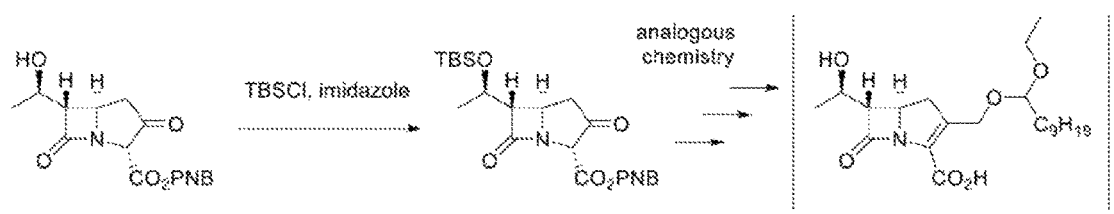
FIG. 6 illustrates an alternative mechanism of synthesis of a meropenem-caged decanal, according to another embodiment.

Here, a reporter system is developed for detecting the presence of carbapenemase in cells. Decanal is the caged molecule, caged by a meropenem-based molecule, resulting in a carbapenem-caged decanal. Approximately 100-200 mg of the decyl acetal of meropenem (i.e., the carbapenem-caged decanal) were synthesized by the scheme shown in FIG. 5. An alternative mechanism of synthesis of the decyl acetal of meropenem without the 1-beta-methyl group is performed as shown in FIG. 6.

To detect the presence of the carbapenemase, an Enterobacteriaceae-based NRTP including a luciferase reporter system is produced (as described in PCT/US2014/026536, Example 1). The NRTP and carbapenem-caged decanal are added to a sample that is suspected of containing Enterobacteriaceae that expresses a carbapenemase. If Enterobacteriaceae is present in the sample, the reporter system causes the expression of bacterial luciferase in the cell. If the cell also expresses a carbapenemase, then the carbapenemase un-cages the decanal molecule and allows it to mediate a luminescence reaction via the expressed bacterial luciferase, causing the production of a detectable luminescent signal. If the cell does not contain the carbapenemase, the system does not produce a detectable signal. In this manner, the system is able to report on the presence of a carbapenemase in the Enterobacteriaceae cell. The reporter assay is also run combined with a carbapenem to determine whether the Enterobacteriaceae is susceptible or non-susceptible to the carbapenem. This system is further used to determine the mechanism involved in carbapenem susceptibility. In the assay, the reporter assay is run to determine if Enterobacteriaceae is present. The reporter assay is also run combined with a carbapenem to determine if the organism is non-susceptible to the carbapenem. The reporter assay is also run using a carbapenem-caged substrate to determine if the organism expresses a carbapenemase.

If the above reporter assay determines that the target organism is present and is non-susceptible to the carbapenem, the reporter assay is performed again combined with various reagents: the assay is run with the carbapenem and a β-lactamase inhibitor such as boronic acid to determine if the non-susceptible organism becomes susceptible in the presence of the β-lactamase inhibitor. The reporter assay is also run with the carbapenem and a chelator such as EDTA to determine if the non-susceptible organism becomes susceptible in the absence of metal.

Table 2 depicts results produced by the assay, where 'x' denotes a positive result by the reporter assay. Sample 1 does not contain the target organism. Sample 2 contains the target organism that is susceptible to the carbapenem and it does not express a carbapenemase. Sample 3 contains the target organism, is non-susceptible to the carbapenem, the β-lactamase inhibitor inhibits the non-susceptible result, the chelator does not inhibit the non-susceptible result, and the organism expresses a carbapenemase; based on these results, the organism likely expresses a Class A carbapenemase. Sample 4 contains the target organism, is non-susceptible to the carbapenem, the β-lactamase inhibitor does not inhibit the non-susceptible result, the chelator does inhibit the non-susceptible result, and the organism expresses a carbapenemase; based on these results, the organism likely expresses a Class B carbapenemase. Sample 5 contains the target organism, is non-susceptible to the carbapenem, the β-lactamase inhibitor does not inhibit the non-susceptible result, the chelator does not inhibit the non-susceptible result, and the organism expresses a carbapenemase; based on these results, the organism may express a Class D carbapenemase or multiple carbapenemases including Class D and Class A or Class B, or Class A and Class B. Sample 6 contains the target organism, is non-susceptible to the carbapenem, the β-lactamase inhibitor does not inhibit the non-susceptible result, the chelator does not inhibit the non-susceptible result, and the organism does not express the carbapenemase; based on these results, the non-susceptible phenotype of the organism may be due to a mechanism such as AmpC over-expression and porin mutations. Sample 7 contains the target organism, is susceptible to the carbapenem and expresses a carbapenemase; based on these results, the organism is a carbapenem-susceptible, carbapenemase-expressing organism. Using the assay described above, the carbapenem susceptibility phenotype of the Enterobacteriaceae in several samples 1-7 was determined.

TABLE 2

Results of carbapenem susceptibility mechanism determination assay

|  | Reporter | Reporter + Antibiotic | Reporter + Antibiotic + Inhibitor | Reporter + Antibiotic + EDTA | Reporter + Reagent | Result |
|---|---|---|---|---|---|---|
| Sample 1 |  | NA | NA | NA | NA | No target cell present |
| Sample 2 | x |  | NA | NA | x | Susceptible |
| Sample 3 | x | x |  | x | x | Non-susceptible, expresses Class A carbapenemase |

TABLE 2-continued

Results of carbapenem susceptibility mechanism determination assay

| | Reporter | Reporter + Antibiotic | Reporter + Antibiotic + Inhibitor | Reporter + Antibiotic + EDTA | Reporter + Reagent | Result |
|---|---|---|---|---|---|---|
| Sample 4 | x | x | x | | x | Non-susceptible, expresses Class B carbapenemase |
| Sample 5 | x | x | x | x | x | Non-susceptible, expresses Class D carbapenemase or Class A & B carbapenemases |
| Sample 6 | x | x | x | x | | Non-susceptible, does not express a carbapenemase |
| Sample 7 | x | | NA | NA | x | Susceptible and expresses carbapenemase |

Further testing includes the addition of cloxacillin as an inhibitor of AmpC-mediated non-susceptibility. In this case, the addition on cloxacillin can allow for confirmation that a carbapenemase is not responsible for the non-susceptibility result of Sample 6 in which case, the addition of cloxacillin would cause Sample 6 to exhibit a non-susceptible result with the addition of the carbapenem.

Example 4: A Novel Systems-Based Molecular Diagnostic for Carbapenem Susceptibility Testing and Resistance Mechanism Determination Background: Carbapenem resistance in Gram-negative bacteria has become a serious clinical issue with limited diagnostic and treatment options. Novel antimicrobials such as the recently approved Avycaz (Actavis), and the in-development Relebactam (Merck) and Carbavance (The Medicines Company) have shown activity against Class A carbapenemases (e.g. KPC) though not against Class B carbapenemases (e.g. NDM-1). Thus, the ability to quickly detect viable Gram-negative bacteria, determine their susceptibility to carbapenems, and distinguish between carbapenem resistance mechanisms could aid physicians in considering such therapeutic options in the future. We have developed Smarticles™ technology, a live cell luminescence assay for detection and susceptibility testing directly from clinical samples, as described herein, e.g., at least at Examples 1-4, and throughout the detailed description. In this study, a Smarticles™ assay was evaluated for its ability to detect carbapenem resistant *E. coli* and distinguish between NDM-1 and KPC-expressing organisms.

Methods: 26 clinical isolates of *E. coli*, *Klebsiella* spp., *Enterobacter* spp., *Citrobacter* spp., *Proteus* spp., and *S. marcescens* were evaluated using the Smarticles™ assay and ertapenem disk diffusion. CRE isolates included organisms expressing blaKPC and blaNDM-1. The Smarticles™ assay was used with the addition of the chelating agent edetic acid (EDTA) and β-lactamase inhibitor boronic acid to scrutinize clinical isolates of *E. coli* expressing NDM-1 and KPC.

Results: The Smarticles™ assay demonstrated the ability to distinguish between ertapenem susceptible and non-susceptible Enterobacteriaceae in 2 hours. The Smarticles™ assay was also able to distinguish between NDM-1 and KPC-expressing *E. coli* where, in the presence of EDTA, the assay signal was inhibited in NDM-1-expressing *E. coli* and not inhibited in KPC-expressing *E. coli* and, in the presence of boronic acid, the assay signal was inhibited in KPC-expressing *E. coli* and not inhibited in NDM-1-expressing *E. coli*.

CONCLUSION

The ability of the Smarticles™ assay to detect carbapenem-resistant bacteria and distinguish among carbapenem-resistance mechanisms has the potential to aid in treatment guidance for novel antibiotics that have been shown to have activity against a targeted group of resistance mechanisms.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed:

1. A kit for determining a mechanism of antimicrobial resistance for a microorganism to an antimicrobial agent comprising:
   an antimicrobial agent, wherein the antimicrobial agent is a compound that kills, inhibits the growth of, or otherwise compromises the viability of the growth of one or more microorganisms;
   a non-replicative transduction particle (NRTP) comprising a reporter nucleic acid molecule encoding a reporter molecule;
   a caged substrate having a structure of

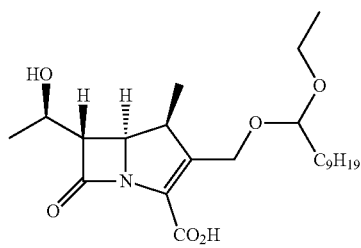

and
   capable of entering the microorganism and becoming an un-caged substrate in the presence of an enzyme related to a mechanism of resistance to the antimicrobial agent, wherein the un-caged substrate reacts with the reporter molecule to produce a detectable signal, wherein detection of the detectable signal confirms a presence of the microorganism in the sample; and instructions for using the antimicrobial agent, the NRTP, and the caged substrate to determine the mechanism of antimicrobial resistance for the microorganism to the antimicrobial agent based on the presence or absence of a detectable indication of viability associated with the microorganism when the microorganism is in contact with the antimicrobial agent, the NRTP and the caged substrate, wherein the presence of a detectable indication of viability indicates that the microorganism is viable and that the enzyme related to the mechanism of resistance to the antimicrobial agent is expressed by the microorganism, and wherein the absence of an indication of viability indicates that the microorganism is not viable and that the enzyme related to the mechanism of resistance to the antimicrobial agent is not expressed by the microorganism.

2. The kit of claim 1, wherein said reporter molecule is expressed from a reporter gene wherein said reporter gene is selected from the group consisting of genes encoding enzymes mediating luminescence reactions and genes encoding enzymes mediating colorimetric reactions.

3. The kit of claim 2, wherein said genes encoding enzymes mediating luminescence reactions comprise genes encoding luciferases.

4. The kit of claim 1, wherein said microorganism is a prokaryote or a eukaryote.

5. The kit of claim 4, wherein said prokaryote is a Gram-negative bacteria or a Gram-positive bacteria.

6. The kit of claim 1, wherein said microorganism is any one of *Staphylococcus* spp., Enterobacteriaceae, *Enterococcus* spp., *Streptococcus* spp., *Acinetobacter* spp., *Pseudomonas* spp., *Stenotrophomonas* spp., *Mycobacterium* spp., or *Candida*.

7. The kit of claim 1, wherein said mechanism of antimicrobial resistance comprises carbapenemase activity.

8. The kit of claim 7, wherein said carbapenemase activity is from a Class A carbapenemase, a Class B carbapenemase, a class D carbapenemase, or a combination thereof.

9. The kit of claim 1, wherein said antimicrobial resistance comprises resistance to a carbapenem.

10. The kit of claim 1, wherein said enzyme is a carbapenemase.

* * * * *